United States Patent
Xu et al.

(10) Patent No.: US 11,482,304 B2
(45) Date of Patent: Oct. 25, 2022

(54) ALIGNMENT METHODS, DEVICES AND SYSTEMS

(71) Applicant: GENEMIND BIOSCIENCES COMPANY LIMITED, Shenzhen (CN)

(72) Inventors: Weibin Xu, Shenzhen (CN); Huan Jin, Shenzhen (CN); Qin Yan, Shenzhen (CN); Zefei Jiang, Shenzhen (CN); Zhiliang Zhou, Shenzhen (CN)

(73) Assignee: GENEMIND BIOSCIENCES COMPANY LIMITED, Shenzhen (CN)

( * ) Notice: Subject to any disclaimer, the term of this patent is extended or adjusted under 35 U.S.C. 154(b) by 0 days.

(21) Appl. No.: 16/635,996

(22) PCT Filed: Aug. 2, 2017

(86) PCT No.: PCT/CN2017/095612
§ 371 (c)(1),
(2) Date: Jan. 31, 2020

(87) PCT Pub. No.: WO2019/023978
PCT Pub. Date: Feb. 7, 2019

(65) Prior Publication Data
US 2020/0381082 A1 Dec. 3, 2020

(51) Int. Cl.
*G01N 33/48* (2006.01)
*G16B 30/10* (2019.01)
*G16B 35/10* (2019.01)

(52) U.S. Cl.
CPC ............. *G16B 30/10* (2019.02); *G16B 35/10* (2019.02)

(58) Field of Classification Search
None
See application file for complete search history.

(56) References Cited

U.S. PATENT DOCUMENTS

| 10,364,468 B2 | 7/2019 | Lee et al. | |
| 2011/0257889 A1 | 10/2011 | Klammer et al. | |
| 2012/0089338 A1* | 4/2012 | Roth | G16B 30/10 702/19 |
| 2014/0114584 A1 | 4/2014 | Bruestle | |
| 2014/0121991 A1 | 5/2014 | Park | |
| 2020/0372031 A1* | 11/2020 | Ruehle | G06F 16/24566 |

FOREIGN PATENT DOCUMENTS

| CN | 103294932 A | 9/2013 |
| CN | 103451279 A | 12/2013 |
| CN | 105243297 A | 1/2016 |
| CN | 106096332 A | 11/2016 |

OTHER PUBLICATIONS

Li, Heng, and Nils Homer. "A survey of sequence alignment algorithms for next-generation sequencing." Briefings in bioinformatics 11.5 (2010): 473-483.*
Xin, Hongyi, et al. "Accelerating read mapping with FastHASH." BMC genomics. vol. 14. No. 1. BioMed Central, 2013.*
Georganas, Evangelos, et al. "meraligner: A fully parallel sequence aligner." 2015 IEEE International Parallel and Distributed Processing Symposium. IEEE, 2015.*
Zaharia, Matei, et al. "Faster and more accurate sequence alignment with SNAP." arXiv preprint arXiv:1111.5572 (2011).*
Likic, Vladimir. "The Needleman-Wunsch algorithm for sequence alignment." Lecture given at the 7th Melbourne Bioinformatics Course, Bi021 Molecular Science and Biotechnology Institute, University of Melbourne (2008): 1-46.*
Georganas, Evangelos, et al. "meraligner: A fully parallel sequence aligner." 2015 IEEE International Parallel and Distributed Processing Symposium. IEEE, 2015, pp. 561-570.*
Rizk et al. "GASSST: global alignment short sequence search tool" *Bioinformatics*, 26:(20), pp. 2534-2540, Oct. 15, 2010.
Xin et al., "Accelerating read mapping with FastHASH," *The Eleventh Asia Pacific Bioinformatics Conference*, Vancouver, Canada, Jan. 21-24, 2013, 13 pages.

\* cited by examiner

*Primary Examiner* — Anna Skibinsky
(74) *Attorney, Agent, or Firm* — Seed IP Law Group LLP (57) ABSTRACT

The disclosure discloses an alignment method, device, and system. The alignment method includes: converting each read into a set of short fragments corresponding to the read to obtain a plurality of sets of short fragments; determining a corresponding position of the short fragment in a reference library to obtain a first positioning result, wherein the reference library is a hash table constructed based on a reference sequence, the reference library includes a plurality of entries, one entry of the reference library corresponds to one seed sequence, and the seed sequence is capable of matching at least one sequence on the reference sequence, a distance between two seed sequences corresponding to two adjacent entries of the reference library on the reference sequence is less than a length of the short fragment; removing a short fragment positioned on any one of the adjacent entries of the reference library in the first positioning result to obtain a second positioning result; and extending based on short fragments from the same read in the second positioning result to obtain an alignment result of the read. The alignment method can efficiently and accurately process and position sequencing data.

21 Claims, 7 Drawing Sheets

ALIGNMENT METHODS, DEVICES AND SYSTEMS

TECHNICAL FIELD

The present disclosure relates to the field of data processing, and more particularly relates to a sequence alignment method, a sequence alignment device, and a sequence alignment system.

BACKGROUND

In biological data processing and analysis, alignment, as a basic part of biological information analysis, puts forward certain requirements on time-consuming and efficiency, and different alignment models and algorithms have different sensitivity and accuracy.

At present, mainstream alignment software, such as Bwa, Bowtie, and SOAP, is mainly developed for sequences generated by the second generation sequencing platform, while the software such as Blast and Mapq is mainly developed for long sequences.

Current alignment methods need to be improved in terms of sensitivity, time-consuming and/or alignment efficiency of specific types of data.

SUMMARY

The embodiments of the present disclosure aim to at least solve one of the technical problems existing in the prior art or to at least provide a commercial means.

According to an aspect of the present disclosure, an alignment method is provided, which includes the following steps of: converting each read into a set of short fragments corresponding to the read to obtain a plurality of sets of short fragments; determining a corresponding position of the short fragment in a reference library to obtain a first positioning result, wherein the reference library is a hash table constructed based on a reference sequence, the reference library includes a plurality of entries, one entry of the reference library corresponds to one seed sequence, and the seed sequence is capable of matching at least one sequence on the reference sequence, a distance between two seed sequences corresponding to two adjacent entries of the reference library on the reference sequence is less than a length of the short fragment; removing a short fragment positioned on any one of the adjacent entries of the reference library in the first positioning result to obtain a second positioning result; and extending based on short fragments from the same read in the second positioning result to obtain an alignment result of the read.

According to another aspect of the present disclosure, an alignment device is provided for implementing all or part of the steps of the aforementioned alignment method, and the device includes a conversion module configured to convert each read into a set of short fragments corresponding to the read to obtain a plurality of sets of short fragments; a searching module configured to determine a corresponding position of the short fragment in a reference library to obtain a first positioning result, wherein the reference library is a hash table constructed based on a reference sequence, the reference library includes a plurality of entries, one entry of the reference library corresponds to one seed sequence, and the seed sequence is capable of matching at least one sequence on the reference sequence, a distance between two seed sequences corresponding to two adjacent entries of the reference library on the reference sequence is less than a length of the short fragment; a culling module configured to remove a short fragment positioned on any one of the adjacent entries of the reference library in the first positioning result to obtain a second positioning result; and a extension module configured to extend based on short fragments from the same read in the second positioning result to obtain an alignment result of the read.

According to yet another aspect of the present disclosure, a computer readable medium is provided for storing/carrying a computer executable program. It will be understood by those skilled in the art that when the program is executed, all or part of the steps of the aforementioned alignment method can be performed by instructing related hardware. The medium may include: a read-only memory, a random access memory, a magnetic disk or an optical disk, and the like.

According to still another aspect of the present disclosure, an alignment system is provided, which includes an input device configured to input data; an output device configured to output data; a processor configured to execute a computer executable program, wherein the executing the computer executable program includes performing the aforementioned method; and a storage device configured to store data. The storage device includes the computer executable program.

The alignment method, device and/or system in accordance with the present disclosure have higher sensitivity and accuracy by converting the read into the short fragment and converting the sequence information into the position information, and can efficiently and accurately process the off-line data of various sequencing platforms, including the off-line data of long-read sequencing and short-read sequencing. In particular, it is particularly suitable for efficient and accurate positioning of reads containing unrecognized bases, i.e., reads containing gaps.

Additional aspects and advantages of the present disclosure will be set forth in part in the following description, which will become apparent from the following description, or may be appreciated by practice of the present disclosure.

BRIEF DESCRIPTION OF THE DRAWINGS

The above and/or additional aspects and advantages of the present disclosure will become apparent and readily appreciated from the following description of the embodiments, taken in conjunction with the accompanying drawings of which.

DETAILED DESCRIPTION OF THE EMBODIMENTS

The embodiments of the present disclosure are described in detail below, and the examples of the embodiments are illustrated in the drawings, wherein identical or similar reference numerals represent identical or similar elements or elements having identical or similar functions. The embodiments described below with reference to the accompanying drawings are exemplary and are intended to be illustrative of the disclosure and not to be construed as limiting the disclosure.

In the description of the present disclosure, the terms "first" and "second" are used for descriptive purposes only, and are not to be construed as indicating or implying relative importance and/or order.

The "connected" and "coupled" used herein are to be understood broadly, and may be, for example, fixedly connected, detachably connected, or integrally connected; can be mechanically or electrically connected; may be connected directly or indirectly through intervening media, or may be internal communication between two elements. The specific meaning of the above terms in the present disclosure can be understood in specific circumstances by those skilled in the art.

The "read" used herein refers to a sequence fragment obtained by sequencing a DNA/RNA/protein sequence, including a sequence obtained by determining and identifying at least a portion of a DNA/RNA/protein sequence using a sequencing platform. The sequencing platform can be selected from, but not limited to, Hisq/Miseq/Nextseq sequencing platform of Illumina, Ion Torrent platform of Thermo Fisher (Life Technologies), BGISEQ platform of BGI, and the single-molecule sequencing platform. The sequencing mode can be either single-end sequencing or paired-end sequencing, and the obtained off-line data is a sequencing and reading fragment called reads.

The "alignment" used herein refers to sequence alignment, including the process of positioning a read to a reference sequence, as well as the process of obtaining a read position/match(mapping) result.

Figure 1:
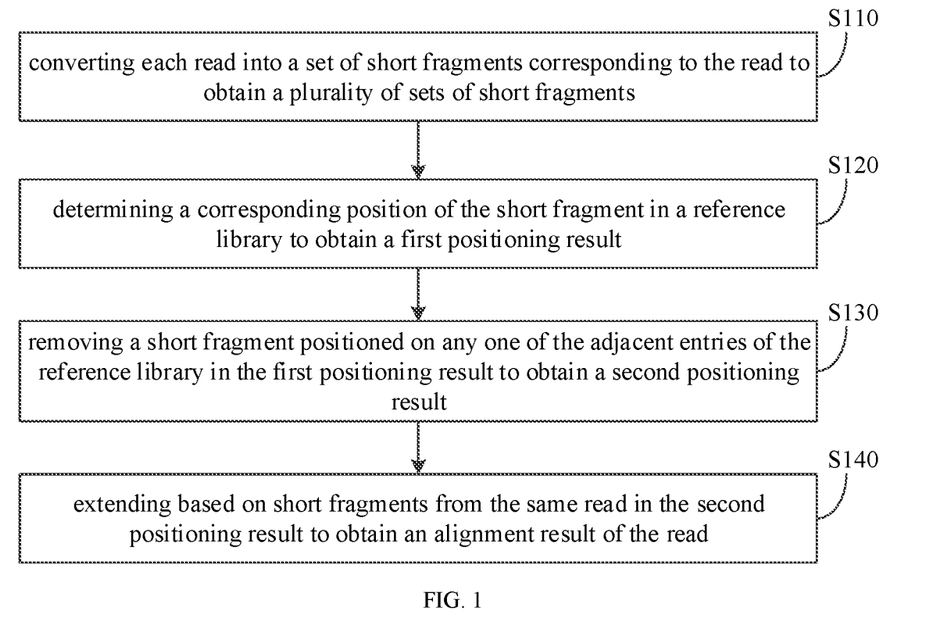
FIG. 1 is a flow chart of an alignment method according to an embodiment of the present disclosure.

Referring to FIG. 1, an alignment method according to an embodiment of the present disclosure includes the following steps: S110, each read is converted into a set of short fragments corresponding to the read to obtain a plurality of sets of short fragments. S120, a corresponding position of the short fragment in a reference library is determined to obtain a first positioning result, the reference library is a hash table constructed based on a reference sequence, the reference library includes a plurality of entries, one entry of the reference library corresponds to one seed sequence, and the seed sequence is capable of matching at least one position on the reference sequence, and a distance between two seed sequences corresponding to two adjacent entries of the reference library on the reference sequence is less than a length of the short fragment. S130, a short fragment positioned on any one of the adjacent entries of the reference library in the first positioning result is removed to obtain a second positioning result. S140, an extension is performed based on short fragments from the same read in the second positioning result to obtain an alignment result of the read. By converting the read into the short fragment and converting the read sequence information into the position information, that is, converting the sequence form into a digital form, the alignment method is favorable for quickly and accurately achieving the alignment and positioning of the off-line data of various sequencing platforms. In particular, it is particularly suitable for quick and accurate alignment of reads containing unrecognized bases, i.e., reads containing gaps or N, such as alignment analysis of reads obtained due to poor sequencing quality, poor base recognition, and the like.

The reference sequence (ref) used herein is a predetermined sequence, which may be a DNA and/or RNA sequence previously assembled by itself, may be a DNA and/or RNA sequence determined and disclosed by others, and may be any previously obtained reference template in a biological category to which a target individual belongs, for example, all or at least a portion of a disclosed genome assembly sequence of the same biological category. If the target individual is a human, its genome reference sequence (also referred to as the reference genome or reference chromosomes) may be selected from HG19 provided by the NCBI database. In addition, a resource library containing more reference sequences can be configured in advance, and before sequence alignment, a closer sequence is selected or determined and assembled as a reference sequence according to factors such as sex, race, region, and the like of the target individual, so that more accurate sequence analysis results can be obtained subsequently. The reference sequence contains the chromosome number and the position information of each site on the chromosome. The reference library used herein is essentially a hash table, and the reference library may be built by directly using the seed sequence used herein as a key (key name) and using the position of the seed sequence used herein on the reference sequence as a value (key value). It is also possible to first convert the seed sequence used herein into a numeric or integer string with the numeric or integer string as the key and the position of the seed sequence on the reference sequence as the value to establish the reference library. The position of the seed sequence on the reference sequence as the value used herein may be the corresponding one or more positions of the seed sequence on the reference sequence/chromosome. The position may be represented directly by a real numerical value or a range of numerical values, and may also be re-encoded to be represented by a custom character and/or number. According to an embodiment of the present disclosure, the construction of the hash table by using a vector of C++ may be expressed as follows: Hash(seed) =Vector(position). The vector used herein is an object entity that can hold many other types of the same element, and is therefore also referred to as a container. The reference library can be built by saving in binary. In addition, the hash table may be divided into blocks for storage, and a block head key and a block tail key are set in the block head. For example, for sequential sequence block {5, 6, 7, 8 . . . , 19, 20}, the block head and the block tail (or a table head and a table tail) 5 and 20 are set, if there is a number of 3, since 3<5, it can be seen that 3 does not belong to the sequential sequence block, and if there is a number of 10, since 5<10<20, it is known that 10 belongs to the sequential sequence block. In this way, the global index can be selected during query, and the block where the global index is located can be quickly located by comparing the block head key and the block tail key without the need of the global index.

The reference library used herein may be built when the sequence is to be aligned, or may be built and stored in advance. According to a specific embodiment of the present disclosure, the reference library is pre-built and stored for use. The building of the reference library includes: a length L of the seed sequence is determined according to total number of bases totalBase of the reference sequence, L=μ*log(totalBase), μ⊂[1,3] and L is less than a length of a read to be aligned and analyzed (read length); all possible seed sequences are generated based on the length of the seed sequence to obtain a seed sequence set; and a seed sequence capable of matching the reference sequence in the seed sequence set and a matching position of the seed sequence are determined to obtain the reference library. Based on the relationship between the length of the seed sequence and the reference sequence established by the inventor through multiple hypothesis test verification, the method enables the built reference library to contain a comprehensive seed sequences with the correlation information of the corresponding positions of the seed sequences on the reference sequence. The reference library has a compact structure and small memory occupation and can be used for high-speed access query in sequence positioning analysis. An entry of the reference library obtained according to this embodiment contains only one key, one key corresponds to at least one value.

This embodiment of the present disclosure is not limited to the method of generating all possible seed sequences and obtaining the seed sequence set. For inputting a set, elements in the set may be traversed to obtain all possible combinations of elements of a specific length, which may be implemented by using a recursive algorithm and/or a loop algorithm, for example.

In one example, the reference sequence is a human genome containing about 3 billion bases, the length of the reads to be processed is not less than 25 bp, and L takes an integer in [11, 15] to facilitate efficient alignment.

In one example, the reference sequence is a human cDNA reference genome, the total number of bases totalBase of the reference genome is counted, and the length L of the seed sequence (seed) is set based on the total number of bases, L(seed)=log(totalBase)*μ, μ⊂[1,3]. Based on the L and the base types of the DNA sequences including A, T, C, and G, a set of all possible seed sequences is generated by using a recursive algorithm to obtain the seed sequence set, which can be represented as seed=$B_1B_2 \ldots B_L$, $B \in \{ATCG\}$. The seed sequence capable of matching the reference genome in the seed sequence set and the matching position of the seed sequence are determined to obtain the reference library, so that the reference library is built and obtained by taking the seed sequences capable of matching the reference genome as the key and the position of the seed sequence on the reference genome as the value.

In one example, the reference sequence is the DNA genome and transcriptome of a species, the total number of bases totalBase of the reference sequence is counted, and the length L of the seed sequence (seed) is set based on the total number of bases, L(seed)=log(totalBase)*μ, μ⊂[1,3]. Based on the L, the base types constituting the DNA sequences including A, T, C, and G, and the base types constituting the RNA sequences including A, U, C, and G, a set of all possible seed sequences is generated by using a recursive algorithm to obtain the seed sequence set, which can be represented as seed=$B_1B_2 \ldots B_L$, $B \in \{ATCG\} \cup \{AUCG\}$. The seed sequence capable of matching the reference sequence in the seed sequence set and the matching position of the seed sequence are determined to obtain the reference library, so that the reference library is built and obtained by taking the seed sequences capable of matching the reference sequence as the key and the position of the seed sequence on the reference sequence as the value.

In one example, the seed sequence can be converted into a string consisting of numeric characters, and the string is used as a key to build a library, so that the speed of accessing the reference library built by the query can be improved. For example, after a seed sequence capable of matching the reference sequence is obtained, the seed sequence is encoded as follows:

$$seed_i = \begin{cases} 00 & i = A \\ 01 & i = T \text{ or } U \\ 10 & i = C \\ 11 & i = G \end{cases}.$$

For example, after the seed sequence set is obtained, the seed sequence in the seed sequence set is encoded, and the base encoding rule may be the same as described above. In addition, the encoding conversion of the same rule may be carried out on the reference sequence, which is favorable for quickly obtaining the corresponding position information of the seed sequences on the reference sequence and improving the speed of accessing and querying the built reference library.

According to a specific embodiment of the present disclosure, the determining the seed sequence capable of matching the reference sequence in the seed sequence set and the matching position of the seed sequence includes: a sliding window is performed on the reference sequence by using a window having a size of L, the seed sequence in the seed sequence set is matched with a window sequence obtained by the sliding window to determine the seed sequence capable of matching the reference sequence in the seed sequence set and the matching position of the seed, and an error tolerance rate for the matching is $\varepsilon_1$. In this way, the corresponding position information of the seed sequence on the reference sequence can be obtained quickly, which facilitates quickly building and obtaining the reference library. The error tolerance rate used herein is a proportion of allowable mismatched bases, and the mismatch is at least one selected from the group consisting of substitution, insertion, and deletion.

In one example, the match used herein is a strict matching, that is, the error tolerance rate $\varepsilon_1$ is zero, and when the seed sequence is exactly identical to one or more sliding window sequences, the position of the sliding window sequence is the corresponding position of the seed sequence on the reference sequence. In another example, the match used herein is an error-tolerant matching, and the error tolerance rate $\varepsilon_1$ is greater than zero. When the proportion of the inconsistency of the bases at the same positions of the seed sequence and one or more sliding window sequences is less than the error tolerance rate, the position of the sliding window sequence is the corresponding position of the seed sequence on the reference sequence. In one example, the corresponding position of the seed sequence on the reference sequence is encoded, and the reference library is built with the encoded characters, such as numeric characters, as values.

In other words, the error tolerance rate $\varepsilon_1$ is not zero, which is equivalent to converting a seed sequence into a group of seed templates allowed by $\varepsilon_1$. For example, if seed=ATCG, and $\varepsilon_1$ is 0.25, that is, one error is allowed in four bases, then the seed template can be ATCG, TTCG, CTCG, GTCG, AACG, ACCG, AGCG, and the like. When the position of seed=ATCG on the reference sequence is determined at the error tolerance rate of 0.25, it is equivalent to determining the positions of all seed templates corresponding to the seed on the reference sequence, for example, ref=ATCG, all the previously shown seed templates may be matched to this position, and ref=TTCG, seed templates ATCG, TTCG, CTCG, or GTCG may be matched to the position. Furthermore, the built reference library may use a seed as a key, or each of all seed templates corresponding to the seed as a key, where the key is different from the key, and one key corresponds to at least one value.

According to a specific embodiment of the present disclosure, when determining the corresponding position of the seed sequence on the reference sequence, a step size of performing the sliding window on the reference sequence is determined in accordance with L and $\varepsilon_1$. In one example, the step size of performing the sliding window is no less than $L*\varepsilon_1$. In a specific example, the reference sequence is a human genome containing about 3 billion bases, the length of the reads to be processed is not less than 25 bp, L is 14 bp, and $\varepsilon_1$ is 0.2-0.3, the step size of performing the sliding window is 3 bp to 5 bp, so that two adjacent windows can stride over continuous error combination under the condition of $\varepsilon_1$ in the positioning process of the sliding window, and rapid positioning is facilitated. In one example, a distance between two adjacent entries of the built reference library is the step size of the sliding window.

According to a specific embodiment of the present disclosure, S110 includes: a sliding window is performed on the read by using a window having a size of L to obtain a set of short fragments corresponding to the read, and a step size of performing the sliding window is 1 bp. In this way, for a piece of reads with a length of K, (K−L+1) pieces of short fragments with a length of L are obtained, the reads are converted into the short fragments, the corresponding position of each short fragment in the reference library is determined by using high-speed access to query the reference library, thereby obtaining the information of the reads corresponding to the short fragments in the reference library.

According to a specific embodiment of the present disclosure, S120 includes: the short fragment is matched with a seed sequence corresponding to an entry of the reference library to determine the position of the short fragment in the reference library, and an error tolerance rate for the matching is $\varepsilon_2$.

In one example, the match used herein is a strict matching, that is, the error tolerance rate $\varepsilon_2$ is zero. When a short fragment is exactly identical to a seed or a seed template corresponding to an entry of the reference library, the position information of the short sequence on the reference library is obtained. In another example, the match used herein is an error-tolerant matching, and the error tolerance rate $\varepsilon_2$ is greater than zero. The position information of the short sequence on the reference library is obtained when the proportion of bases in which the short sequence does not match the seed or the seed template corresponding to one or more entries of the reference library is less than the error tolerance rate. In a specific example, $\varepsilon_2=\varepsilon_1$ and not zero, enabling more valid data to be obtained.

Figure 2:
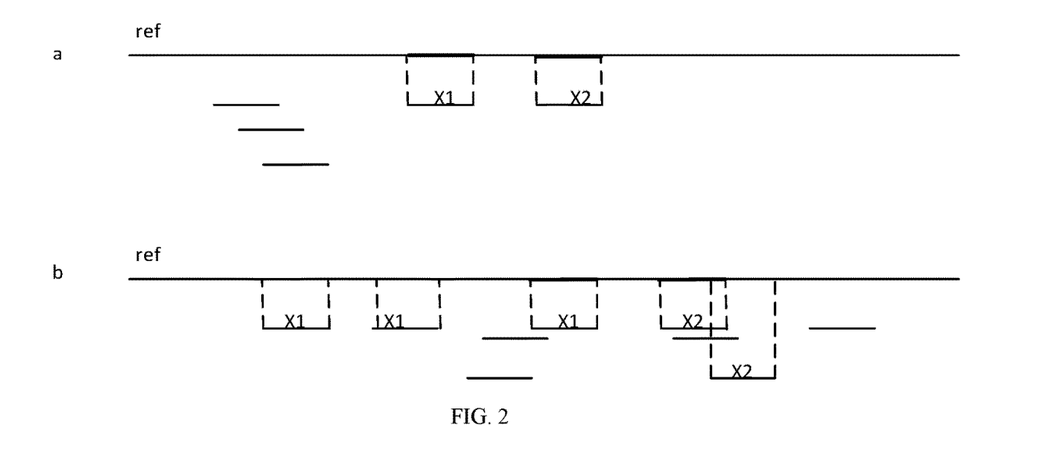
FIG. 2 is a schematic view of a distance between two adjacent entries of a reference library according to an embodiment of the present disclosure.

According to a specific embodiment of the present disclosure, referring to FIG. 2, at S120, the distance between the two seed sequences X1 and X2 corresponding to the two adjacent entries of the reference library used herein on the reference sequence ref may be divided into the following two cases. When the keys and values of the two entries of the reference library are both unique, that is, one entry corresponds to one [key, value], and referring to FIG. 2a, which is equivalent to when X1 and X2 are uniquely matched with the reference sequence (both X1 and X2 match only one position of the reference sequence), the distance used herein is a distance between the two positions corresponding to X1 and X2 on the reference sequence, and the two positions are shown in the bold black lines. When the key of at least one of the two entries of the reference library corresponds to multiple values, referring to FIG. 2b, which is equivalent to that at least one of the two seed sequences X1 and X2 and the reference sequence are non-uniquely matched, that is, at least one of X1 and X2 matches multiple positions of the reference sequence, the distance used herein is a distance between the two closest positions on the reference sequence corresponding to the X1 and X2, and the two positions are shown in bold black lines. The method of expressing the distance between two sequences in this embodiment is not limited, and may be expressed as, for example, a distance from any one of the both ends of one sequence to any one of the ends of the other sequence, or a distance from the center of one sequence to the center of the other sequence.

According to a specific embodiment of the present disclosure, after the second positioning result is obtained, S130 further includes: a short fragment having a connectivity length less than a predetermined threshold is removed, and the second positioning result is replaced with a removed result. The connectivity length is a total length of short fragments in the second alignment result that are from the same read and are positioned to different entries of the reference library mapped to the reference sequence. This process facilitates the removal of some data that is transitionally redundant and/or of relatively low quality, facilitating an increase in speed of alignment.

Figure 3:
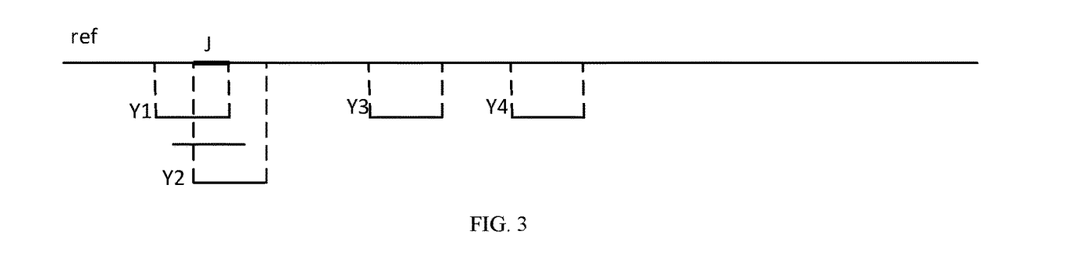
FIG. 3 is a schematic view of a connectivity length according to an embodiment of the present disclosure.

The connectivity length may be expressed as a sum of the lengths of the short fragments from the same read and positioned to different entries of the reference library minus the length of the overlapping portion of the short fragments mapped onto the reference sequence. In one example, there are four short fragments from one read and positioned to different entries of the reference library, denoted as Y1, Y2, Y3, and Y4, each having a length of L1, L2, L3, and L4, respectively. The positioning positions are shown schematically in FIG. 3, where X1 and X2 are mapped to the reference sequence with overlapping positions, the length of the overlapping positions is J, and the connectivity length is (L1+L2+L3+L4−J). In one example, the different short fragments are all L in length, and the predetermined threshold used herein is L, so that the alignment speed can be increased while allowing for the loss of data that is partially valid but of relatively low quality.

According to a specific embodiment of the present disclosure, after the second positioning result is obtained, S130 further includes: according to a positioning result of a short fragment from the same read in the second positioning result, a positioning result of the read is determined, and a read whose determination result does not meet a predetermined requirement is removed. The read is removed and the short fragment corresponding to the read is also removed. Therefore, on the premise of satisfying a certain sensitivity and specificity, an accurate mapping/local quick alignment can be directly carried out on the basis of the second positioning result, which can accelerate the alignment.

The evaluation method is not limited in this embodiment, and for example, a quantitative scoring method may be used. In one example, the positioning results of short fragments from the same read are scored, with the scoring rule being: the sites matching the reference sequence are added a negative number, and the sites not matching the reference sequence are added a positive number. After the second positioning result is obtained, according to the positioning result of the short fragment from the same read in the second positioning result, the positioning result of the read is scored, and a read having a score no greater than a first preset value is removed. According to a specific example, the read length is 25 bp, and sequence construction is performed on the short fragments from the same read to obtain a reconstructed sequence. For example, the base type of a certain site can be determined according to the support of more short sequences, if a certain site has no short fragment supported, namely no short fragment is aligned to the site, the base type of the site is uncertain and can be represented by N, so that a reconstructed sequence is obtained. It can be seen that the reconstructed sequence corresponds to the read, and the length of the reconstructed sequence is the read length. The site where the reconstructed sequence matches the reference sequence (ref) is subtracted by one, and the site where the reconstructed sequence does not match the reference sequence is added by one. The alignment error tolerance rate, namely the allowed mismatch ratio for one read/reconstructed sequence is 0.12, the length of the alignment allowable error is 3 bp (25×0.12), an initial score $Score_{init}$ is the read length, and the first preset value is 22 (25−3). In this way, reconstructed sequences whose score is less than 22, that is, the proportion of sites that do not match the reference sequence exceeds the alignment error tolerance rate are removed, which facilitates speeding up the alignment while allowing for the loss of data that is partially valid but of relatively low quality. According to a specific example, using bit arithmetic and dynamic programming algorithms [G. Myers. A fast bit-vector algorithm for approximate string matching based on dynamic progamming. Journal of the ACM, 46(3): 395-415, 1999], for each reconstructed sequence, the position of each site i is read in, a fast matching scoring is performed using a 64-bit binary mask, one point for each site, an initial Score $Score_{init}$ is the read length, which can be expressed as $Score_{init}$=length (read), and the score Score is obtained by the matching scoring, which can be expressed as $$Score = \begin{cases} -1 & read[i] = ref[j], j \subset (i-1, i+1) \\ +1 & read[i] != ref[j], j \subset (i-1, i+1) \end{cases}.$$

In one example, the positioning results of short fragments from the same read are scored, with the scoring rule being: the sites matching the reference sequence are added a positive number, and the sites not matching the reference sequence are added a negative number. After the second positioning result is obtained, according to the positioning result of the short fragment from the same read in the second positioning result, the positioning result of the read is scored, and a short fragment corresponding to a read having a score no less than a second preset value is removed. According to a specific example, the read length is 25 bp, and sequence construction is performed on the short fragments from the same read to obtain a reconstructed sequence. For example, the base type of a certain site can be determined according to the support of more short sequences, if a certain site has no short fragment supported, namely no short fragment is aligned to the site, the base type of the site is uncertain and can be represented by N, so that a reconstructed sequence is obtained. It can be seen that the reconstructed sequence corresponds to the read, and the length of the reconstructed sequence is the read length. The site where the reconstructed sequence matches the reference sequence (ref) is added by one, and the site where the reconstructed sequence does not match the reference sequence is subtracted by one. The alignment error tolerance rate, namely the allowed mismatch ratio for one read/reconstructed sequence is 0.12, the length of the alignment allowable error is 3 bp (25×0.12), an initial score $Score_{init}$ is −25, and the second preset value is −22 (−25−3). In this way, reconstructed sequences whose score is greater than −22 are removed, which facilitates speeding up the alignment while allowing for the loss of data that is partially valid but of relatively low quality.

According to a specific embodiment of the present disclosure, the extending based on short fragments from the same read in the second positioning result at S140 includes: a sequence construction is performed based on the short fragments from the same read to obtain a reconstructed sequence, and the extending is performed based on a common part of the reconstructed sequence and a reference sequence corresponding to the reconstructed sequence to obtain an extension sequence. In this way, the short fragment and the positioning information of the short fragment are converted into the positioning information of the read corresponding to the short fragment (referred to as the reconstructed sequence herein), which facilitates the subsequent alignment processing to be performed quickly and accurately.

The common part used herein is the part common to multiple sequences. According to a specific embodiment of the present disclosure, the common part is referred to as a common substring and/or a common subsequence. The common substring refers to a contiguous part that is common to the plurality of sequences, and the common subsequence needs not be contiguous. For example, for ABCBDAB and BDCABA, the common subsequence is BCBA and the common substring is AB.

In one example, the performing the sequence construction based on the short fragments from the same read to obtain the reconstructed sequence used herein can determine the base type of a certain site on the reconstructed sequence according to the support of more short fragments, and if the short fragments which are not supported by a certain position. If a certain site has no short fragment supported, namely no short fragment is aligned to the site of the reference sequence, the base type of the site is uncertain and can be represented by N, so that the reconstructed sequence is obtained. It can be seen that the reconstructed sequence corresponds to the read, and the length of the reconstructed sequence is the read length.

The reference sequence corresponding to the reconstructed sequence used herein is a reference sequence matched with the reconstructed sequence, and the length of the reference sequence is no less than the read length. In one example, the length of the reference sequence corresponding to the reconstructed sequence is the same as that of the reconstructed sequence, and both are read length. In another example, the reconstructed sequence is allowed to be matched with the corresponding reference sequence in an error-tolerant manner, the length of the reference sequence corresponding to the reconstructed sequence is the length of the reconstructed sequence plus two times of the error-tolerant matching length. For example, the length of the reconstructed sequence, i.e., the read length, is 25 bp, the matching of the reconstructed sequence and the reference sequence is allowed to be mismatched by 12%, and the reference sequence aligned to the reconstructed sequence and the sequence of 3 bp (25×12%) at both ends of the reference sequence can be used as the reference sequence corresponding to the reconstructed sequence.

According to a specific example of the present disclosure, the common part is referred to as a common substring. The extending based on short fragments from the same read in the second positioning result at S140 includes: a common substring of the reconstructed sequence and the reference sequence corresponding to the reconstructed sequence is found, and a longest common substring of the reconstructed sequence and the reference sequence corresponding to the reconstructed sequence is determined; and the longest common substring is extended based on an edit distance to obtain an extension sequence. In this way, alignment results containing longer mapping sequences can be obtained more accurately.

According to a specific example of the present disclosure, the common part is referred to as a common subsequence. The extending based on short fragments from the same read in the second positioning result at S140 includes: a common subsequence of the reconstructed sequence and the reference sequence corresponding to the reconstructed sequence is found, and a longest common subsequence of the reconstructed sequence and the reference sequence corresponding to the reconstructed sequence is determined; and the longest common subsequence is extended based on an edit distance to obtain an extension sequence.

The edit distance used herein, also known as Levenshtein distance, refers to the minimum number of editing operations required to change from one to another between two strings. Editing operations include replacing a character with another, inserting a character, and deleting a character. Generally, the smaller the edit distance, the greater the similarity between the two strings.

In one example, for a reconstructed sequence/read, finding the longest common substring of the reconstructed sequence and the reference sequence corresponding to the reconstructed sequence can be expressed as solving the common substring of the two strings $x_1 x_2 \ldots x_i$ and $y_1 y_2 \ldots y_j$, the length of which is m and n, respectively; and calculating the length of the common substring of the two strings to obtain a transfer equation:

$$c[i, j] = \begin{cases} 0 & i = 0 \text{ or } j = 0 \\ c[i-1, j-1] + 1 & x_i = y_j \\ 0 & x_i \neq y_j \end{cases}.$$

The equation is solved to obtain the length of the longest common substring of the two sequences as max(c[i, j]), $i \in \{1, \ldots, m\}$, $j \in \{1, \ldots, n\}$. Then, the longest common substring is converted into the corresponding reference sequence by using the edit distance, so that both ends of the longest common substring can continuously grow, and the minimum character operations (replacement, deletion, and insertion) required between the two strings are found. The edit distance can be determined using a dynamic programming algorithm, the problem has an optimal substructure. The calculation of the edit distance d[i,j] can be expressed as the following formula:

$$d[i, j] = \begin{cases} 0 & i = 0 \text{ or } j = 0 \\ \min(d[i-1, j] + \text{gap}, d[i, j-1] + \text{gap}, \\ \quad d[i-1, j-1] + \text{match}) & x_i = y_j \\ \min(d[i-1, j] + \text{gap}, d[i, j-1] + \text{gap}, \\ \quad d[i-1, j-1] + \text{mismatch}) & x_i \neq y_j \end{cases}.$$

Hole/Gap indicates the insertion or deletion of a character, and the gap in the formula indicates the penalty point required for inserting or deleting a character (corresponding to a site in the sequence). Match indicates that two characters are the same, and the match in the formula indicates a score when two characters are the same. Mismatch indicates that two characters are not equal/different, and the mismatch in the formula indicates a score when two characters are not equal/different. d[i,j] takes the smallest of the three. In a specific example, a gap penalty of 3 points, a consecutive gap increase penalty of 1 point, a site mismatch penalty of 2 points, and a site match score of 0. In this way, it is advantageous to the efficient alignment of gap-containing sequences.

According to a specific embodiment of the present disclosure, the common part is referred to as a common subsequence. According to a specific embodiment of the present disclosure, S140 includes: a common subsequence of the short fragment positioned to the same entry of the reference library in the second positioning result is found, and a longest common subsequence corresponding to each read is determined; and the longest common subsequence is extended based on an edit distance to obtain an extension sequence.

In one example, for a reconstructed sequence/read, the longest common subsequence of the reconstructed sequence and the reference sequence corresponding to the reconstructed sequence is found. Based on the longest common subsequence, the reconstructed sequence corresponding to the longest common subsequence is converted into the reference sequence corresponding to the longest common subsequence. The edit distance of the two sequences can be found out by utilizing Smith Waterman algorithm. For the two strings $x_1 x_2 \ldots x_i$ and $y_1 y_2 \ldots y_j$, it can be obtained by the following formula:

$$F[i, j] = \max \begin{cases} 0 & i = 0 \text{ or } j = 0 \\ F(i-1, j-1) + \sigma(i, j) \\ F(i-1, j) + \sigma(-, j) \\ F(i, j-1) + \sigma(i, -) \end{cases}.$$

σ represents a scoring function, $\sigma(i,j)$ represents the score of the mismatch or match of the characters (sites) $x_i$ and $y_j$, $\sigma(-, j)$ represents the score for vacancy (deletion) of $x_i$ or insertion of $y_j$, and $\sigma(i, -)$ represents the score for deletion of $y_j$ or insertion of $x_i$. Then, the method of calculating the edit distance in the previous example can be used to convert the segment of the reconstructed sequence corresponding to the longest common subsequence into the reference sequence corresponding to the reconstructed sequence, and the segment of the reconstructed sequence corresponding to the longest common subsequence can be continuously grown at both ends to find out the minimum character operation (replacement, deletion, insertion). In a specific example, a gap penalty of 3 points, a consecutive gap increase penalty of 1 point, a site mismatch penalty of 2 points, and a site match score of 4 points. In this way, efficient alignment of gap-containing sequences can be achieved and sequences containing both gaps and other sites with high accuracy can be retained.

According to a specific embodiment of the present disclosure, S140 further includes: the extension sequence is truncated from at least one end of the extension sequence, a proportion of error positioning sites of a truncated extension sequence is calculated, and the truncation is stopped when the following condition is satisfied: the proportion of the error positioning sites of the truncated extension sequence is less than a third preset value. In this way, by using the truncation and culling methods, the local sequence with good matching can be well reserved, which is conducive to improving the efficiency of the data.

Specifically, according to a specific embodiment of the present disclosure, the extension sequence is truncated based on the following: i. a first error rate and a second error rate are calculated; if the first error rate is less than the second error rate, the extension sequence is truncated from a first end of the extension sequence, and if the first error rate is greater than the second error rate, the extension sequence is truncated from a second end of the extension sequence to obtain a truncated extension sequence. The first error rate used herein is a proportion of error positioning sites of the truncated extension sequence obtained by truncating the extension sequence from the first end of the extension sequence, and the second error rate used herein is a proportion of error positioning sites of the truncated extension sequence obtained by truncating the extension sequence from the second end of the extension sequence. ii) i) is performed by replacing the extension sequence with the truncated extension sequence until the proportion of the error positioning sites of the truncated extension sequence is less than a fourth preset value. In this way, by using the double-end truncation and culling methods, the local sequence with good matching can be well reserved, which is conducive to improving the efficiency of the data. According to a specific example, the length of the extension sequence is 25 bp, and the fourth preset value and the third preset value are 0.12.

According to a specific embodiment of the present disclosure, S140 further includes: a sliding window is performed on the extension sequence from at least one end of the extension sequence, and a proportion of error positioning sites of a window sequence obtained by the sliding window is calculated; and the extension sequence is truncated according to the proportion of the error positioning sites of the window sequence, and the truncation is stopped when the following condition is satisfied: the proportion of the error positioning sites of the window sequence obtained by the sliding window is greater than a fifth preset value. In this way, by using the truncation and culling methods, the local sequence with good matching can be well reserved, which is conducive to improving the efficiency of the data.

Specifically, according to a specific embodiment of the present disclosure, the extension sequence is truncated based on the following: i. a third error rate and a fourth error rate are calculated; if the third error rate is less than the fourth error rate, the extension sequence is truncated from a second end of the extension sequence, and if the third error rate is greater than the fourth error rate, the extension sequence is truncated from a first end of the extension sequence to obtain a truncated extension sequence. The third error rate used herein is a proportion of error positioning sites of a window sequence obtained by performing window sliding on the extension sequence from the first end of the extension sequence, and the fourth error rate used herein is a proportion of error positioning sites of a window sequence obtained by performing window sliding on the extension sequence from the second end of the extension sequence. ii) i) is performed by replacing the extension sequence with the truncated extension sequence until the proportion of the error positioning sites of the truncated extension sequence is less than a sixth preset value. In this way, by using the double-end truncation and culling methods, the local sequence with good matching can be well reserved, which is conducive to improving the efficiency of the data.

According to a specific embodiment of the present disclosure, the window of the sliding window is no greater than the length of the extension sequence. According to a specific example, the length of the extension sequence is 25 bp, the window size of the sliding window is 10 bp, and the sixth preset value and the fifth preset value are 0.12.

According to a specific embodiment of the present disclosure, the truncation has a size of 1 bp, that is, one truncation is to remove one base. In this way, the alignment results containing more long sequences can be obtained efficiently.

In a specific example, sequence alignment is performed on the same batch of simulated data using Bowtie (http://bowtie-bio.sourceforge.net/index.shtml), BWA (http://bio-bwa.sourceforge.net/), and the aforementioned alignment method, in which the simulated data is based on the human reference genome setting and contains 100K sequences with a length of 100 bp. The space, time, proportion of reference sequences on the alignment (Map rate), and accuracy required for each software/method run are comparable. In this example, the time and memory required by using the alignment method in this embodiment is slightly longer and greater than those of Bowtie or BWA, but the alignment accuracy and the proportion on sequence alignment by using the alignment method in this embodiment is 98.9% and 99.9%, both slightly higher than those using Bowtie and BWA.

Figure 4:
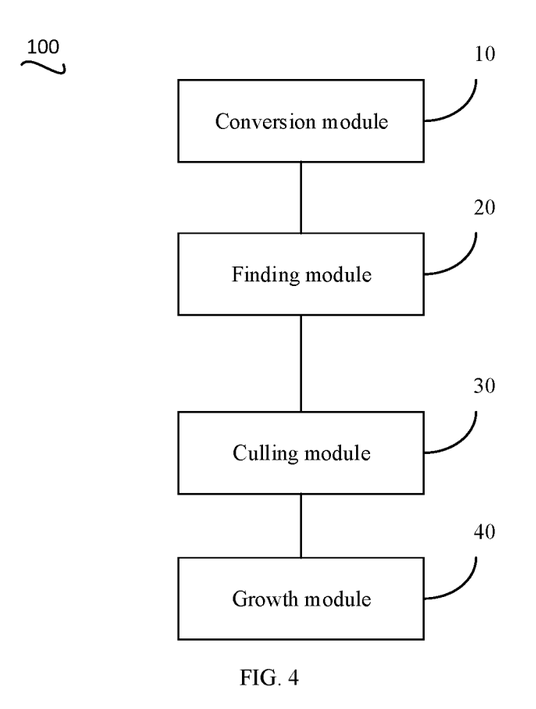
FIG. 4 is a schematic view of an alignment device according to an embodiment of the present disclosure.

Referring to FIG. 4, an alignment device according to an embodiment of the present disclosure includes is provided. The device is configured to implement the method in any one of the aforementioned embodiments/implementations, and the device 100 includes a conversion module 10 configured to convert each read into a set of short fragments corresponding to the read to obtain a plurality of sets of short fragments, a searching module 20 configured to determine a corresponding position of the short fragment in a reference library to obtain a first positioning result. The reference library is a hash table constructed based on a reference sequence. The reference library includes a plurality of entries, one entry of the reference library corresponds to one seed sequence, and the seed sequence is capable of matching at least one sequence on the reference sequence. A distance between two seed sequences corresponding to two adjacent entries of the reference library on the reference sequence is less than a length of the short fragment. The device further includes a culling module 30 configured to remove a short fragment positioned on any one of the adjacent entries of the reference library in the first positioning result to obtain a second positioning result, and a extension module 40 configured to extend based on short fragments from the same read in the second positioning result to obtain an alignment result of the read.

The foregoing description of the technical features and effects of the alignment method in any one of the embodiments of the present disclosure is also applicable to the alignment device in this embodiment of the present disclosure, and details are not described herein again.

Figure 5:
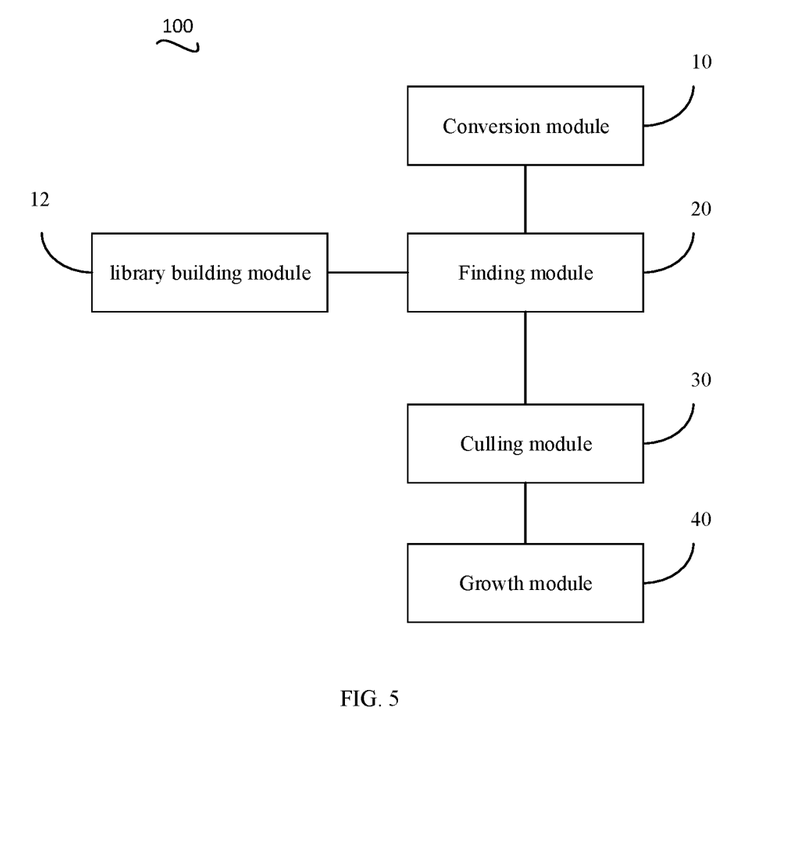
FIG. 5 is a schematic view of an alignment device according to an embodiment of the present disclosure.

For example, according to a specific embodiment of the present disclosure, referring to FIG. 5, the device 100 further includes a library building module 12 configured to build the reference library and to perform the following by using the library building module 12: a length L of the seed sequence is determined according to total number of bases totalBase of the reference sequence, $L=\mu*\log(totalBase)$, $\mu \subset [1,3]$; all possible seed sequences are generated based on the length of the seed sequence to obtain a seed sequence set; and a seed sequence capable of matching the reference sequence in the seed sequence set and a matching position of the seed sequence are determined to obtain the reference library.

According to a specific embodiment of the present disclosure, the determining the seed sequence capable of matching the reference sequence in the seed sequence set and the matching position of the seed sequence includes: a sliding window is performed on the reference sequence by using a window having a size of L, the seed sequence in the seed sequence set is matched with a window sequence obtained by the sliding window to determine the seed sequence capable of matching the reference sequence in the seed sequence set and the matching position of the seed, and an error tolerance rate for the matching is $\varepsilon_1$.

According to a specific embodiment of the present disclosure, a step size of performing the sliding window is determined in accordance with L and $\varepsilon_1$.

According to a specific embodiment of the present disclosure, a step size of performing the sliding window is no less than $L*\varepsilon_1$.

According to a specific embodiment of the disclosure, a distance between two adjacent entries of the reference library is greater than a step size of the sliding window.

According to a specific embodiment of the present disclosure, the conversion module 10 is configured to perform a sliding window on the read by using a window having a size of L to obtain a set of short fragments corresponding to the read, and a step size of performing the sliding window is 1 bp.

Figure 6:
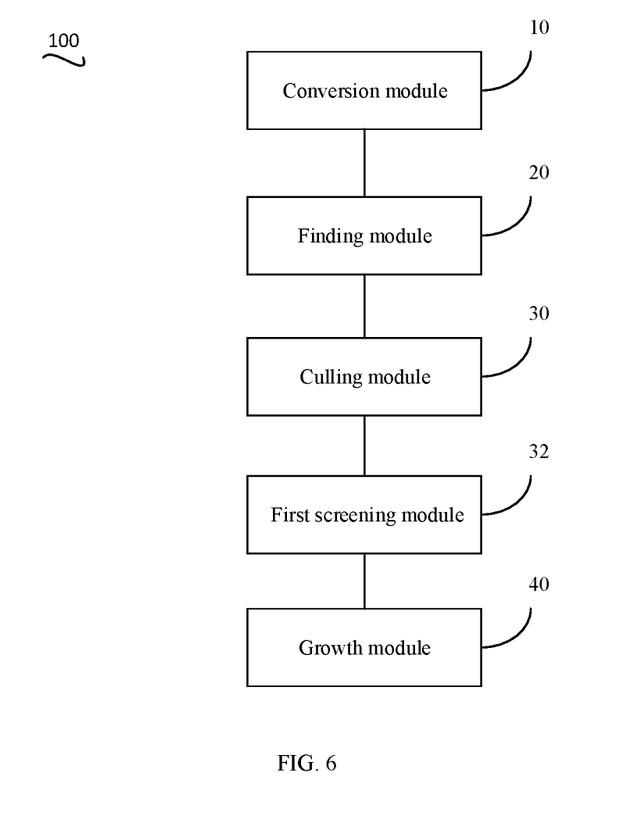
FIG. 6 is a schematic view of an alignment device according to an embodiment of the present disclosure.

According to a specific embodiment of the present disclosure, referring to FIG. 6, a first screening module 32 is further included. The first screening module 32 is coupled to the culling module 30 and configured to perform the following on the second positioning result from the culling module 30: removing a short fragment having a connectivity length less than a predetermined threshold, and replacing the second positioning result with a removed result. The connectivity length is a total length of short fragments in the second alignment result that are from the same read and are positioned to different entries of the reference library mapped to the reference sequence.

Figure 7:
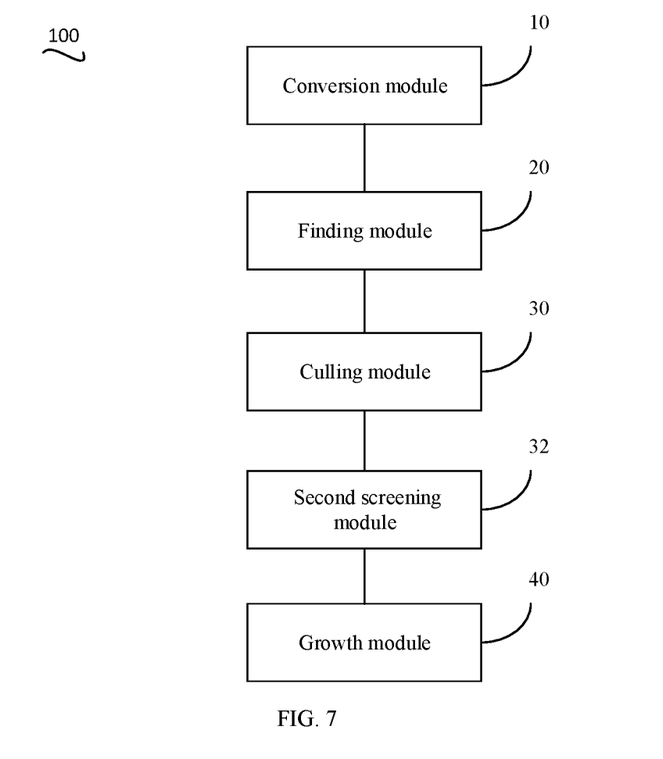
FIG. 7 is a schematic view of an alignment device according to an embodiment of the present disclosure.

According to a specific embodiment of the present disclosure, referring to FIG. 7, a second screening module 34 is further included. The second screening module 34 is coupled to the removal module 30 and configured to determine a positioning result of the read according to a positioning result of a short fragment from the same read in the second positioning result, and remove a short fragment corresponding to a read whose determination result does not meet a predetermined requirement.

According to a specific embodiment of the present disclosure, the second screening module 34 is configured to score the positioning result of the read according to the positioning result of the short fragment from the same read in the second positioning result, and remove a read having a score no greater than a first preset value.

According to a specific embodiment of the present disclosure, the second screening module 34 is configured to score the positioning result of the read according to the positioning result of the short fragment from the same read in the second positioning result, and remove a read having a score no less than a second preset value.

According to a specific embodiment of the present disclosure, the extension module 40 is configured to perform a sequence construction based on the short fragments from the same read to obtain a reconstructed sequence; and extend based on a common part of the reconstructed sequence and a reference sequence corresponding to the reconstructed sequence to obtain an extension sequence.

According to a specific embodiment of the present disclosure, the common part is a common substring. The extension module 40 is configured to find a common substring of the reconstructed sequence and the reference sequence corresponding to the reconstructed sequence, and determine a longest common substring of the reconstructed sequence and the reference sequence corresponding to the reconstructed sequence; and extend the longest common substring based on an edit distance to obtain an extension sequence.

According to a specific embodiment of the present disclosure, the common part is a common subsequence. The extension module 40 is configured to find a common subsequence of the reconstructed sequence and the reference sequence corresponding to the reconstructed sequence, and determine a longest common subsequence of the reconstructed sequence and the reference sequence corresponding to the reconstructed sequence; and extend the longest common subsequence based on an edit distance to obtain an extension sequence.

Figure 8:
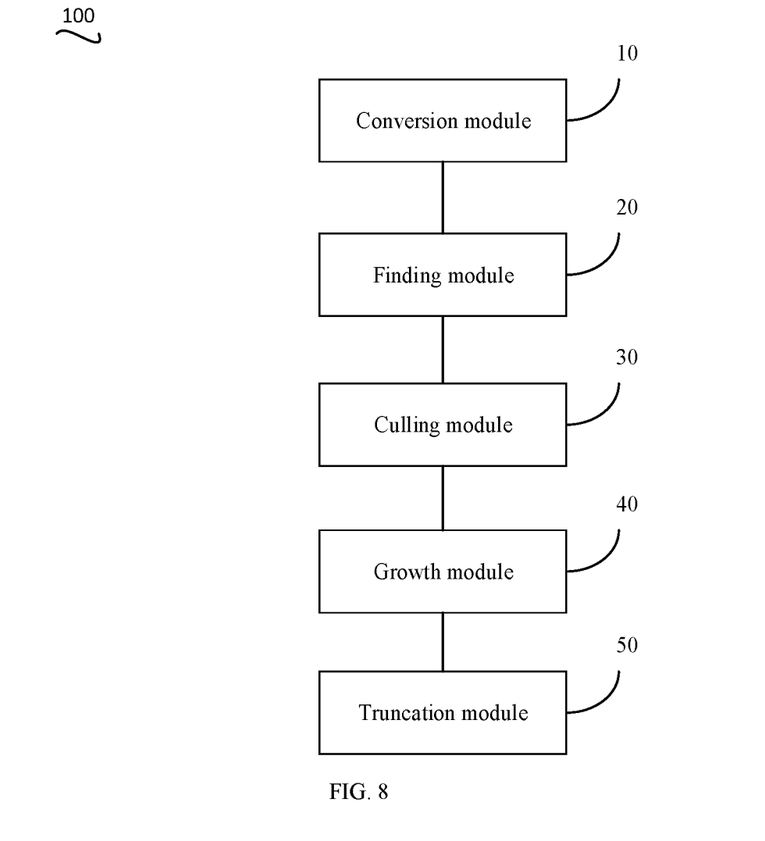
FIG. 8 is a schematic view of an alignment device according to an embodiment of the present disclosure.

According to a specific embodiment of the present disclosure, referring to FIG. 8, a truncation module 50 is further provided, which is configured to truncate the extension sequence from at least one end of the extension sequence from the extension module 40, calculate a proportion of error positioning sites of a truncated extension sequence, and stop the truncation when the following condition is satisfied: the proportion of the error positioning sites of the truncated extension sequence is less than a third preset value.

According to the specific embodiment of the present disclosure, a truncation module 50 is further included and is configured to: i) calculate a first error rate and a second error rate; if the first error rate is less than the second error rate, truncate the extension sequence from a first end of the extension sequence to obtain a truncated extension sequence, and if the first error rate is greater than the second error rate, truncate the extension sequence from a second end of the extension sequence to obtain a truncated extension sequence, wherein the first error rate is a proportion of error positioning sites of the truncated extension sequence obtained by truncating the extension sequence from the first end of the extension sequence, and the second error rate is a proportion of error positioning sites of the truncated extension sequence obtained by truncating the extension sequence from the second end of the extension sequence; and ii) perform i) by replacing the extension sequence with the truncated extension sequence until the proportion of the error positioning sites of the truncated extension sequence is less than a fourth preset value.

According to the specific embodiment of the present disclosure, a truncation module 50 is further included and is configured to perform a sliding window on the extension sequence from at least one end of the extension sequence, and calculate a proportion of error positioning sites of a window sequence obtained by the sliding window, and truncate the extension sequence according to the proportion of the error positioning sites of the window sequence, and stop the truncation when the following condition is satisfied: the proportion of the error positioning sites of the window sequence obtained by the sliding window is greater than a fifth preset value.

According to the specific embodiment of the present disclosure, a truncation module 50 is further included and is configured to: i) calculate a third error rate and a fourth error rate; if the third error rate is less than the fourth error rate, truncate the extension sequence from a second end of the extension sequence to obtain a truncated extension sequence, and if the third error rate is greater than the fourth error rate, truncate the extension sequence from a first end of the extension sequence to obtain a truncated extension sequence, wherein the third error rate is a proportion of error positioning sites of a window sequence obtained by performing window sliding on the extension sequence from the first end of the extension sequence, and the fourth error rate is a proportion of error positioning sites of a window sequence obtained by performing window sliding on the extension sequence from the second end of the extension sequence; and ii) perform i) by replacing the extension sequence with the truncated extension sequence until the proportion of the error positioning sites of the window sequence is greater than the sixth preset value.

According to a specific embodiment of the present disclosure, the truncation has a size of 1 bp.

According to a specific embodiment of the present disclosure, the window of the sliding window is no greater than a length of the extension sequence.

A computer readable medium is provided according to an embodiment of the present disclosure, and the medium is configured to carry a part or all of the steps of the alignment method in any one of the foregoing embodiments. The medium used herein includes, but is not limited to, a read-only memory, a random access memory, a magnetic disk or an optical disk, and the like.

According to an embodiment of the present disclosure, an alignment system is provided, and the system 1000 includes an input device 100 configured to input data; an output device 200 configured to output data; a processor 300 configured to execute a computer executable program, and the executing the computer executable program includes performing the alignment of any one of the foregoing embodiments. The system further includes a storage device 400 configured to store data. The storage device 400 includes the computer executable program.

In the description herein, references to the description of the term "one embodiment", "some embodiments", "an example", "a specific example", or "some examples", etc., mean that a particular feature, structure, material, or characteristic described in connection with the embodiment or example is included in at least one embodiment or example of the disclosure. In this specification, a schematic representation of the foregoing terms does not necessarily refer to the same embodiments or examples. Furthermore, the particular features, structures, materials, or characteristics described may be combined in any suitable manner in any one or more embodiments or examples.

Although embodiments of the present disclosure have been shown and described, it will be understood by those of ordinary skill in the art that various changes, modifications, substitutions and alterations can be made to these embodiments without departing from the principles and spirit of the present disclosure, the scope of the present disclosure being defined by claims and their equivalents.

What is claimed is:

1. A computer-implemented alignment method, comprising:

converting a read into a set of short fragments corresponding to the read;

accessing a reference library residing in a memory coupled with one or more processors, wherein the reference library is a hash table constructed based at least partly on a reference sequence, the reference library comprises a plurality of entries, each entry of the reference library corresponds to a respective seed sequence, each seed sequence is capable of matching at least one sequence on the reference sequence, and representations of individual seed sequences are used as keys for the hash table to map to matching positions on the reference sequence, wherein each seed sequence has a length L according to a total number of bases totalBase of the reference sequence, $L=\mu*\log(totalBase)$, $\mu \subset [1, 3]$, wherein a matching position of each seed sequence is determined by at least performing a sliding window on the reference sequence with a window having a size of L, and wherein a distance on the reference sequence between two seed sequences that correspond to two adjacent entries of the reference library is less than a length of a short fragment;

generating a positioning result based at least partly on the accessed reference library, by at least inputting a representation of each short fragment of the set of short fragments as a key value to the hash table to retrieve a corresponding position on the reference sequence;

modifying the positioning result by removing a subset of short fragments from the set of short fragments, wherein each removed short fragment is selected from a respective group of short fragments in the set, whose positions correspond to adjacent entries of the reference library; and reconstructing a sequence based at least partly on the short fragments from the modified positioning result and their corresponding positions on the reference sequence, to obtain an alignment result of the read.

2. A method as claimed in claim 1, wherein the reference library is constructed by at least:

generating all possible seed sequences based on the length L to obtain a seed sequence set; and generating the reference library by determining a matching position of the seed sequence for each seed sequence capable of matching the reference sequence in the seed sequence set.

3. A method as claimed in claim 2, wherein the determining matching position for each seed sequence capable of matching the reference sequence in the seed sequence set comprises:

matching the seed sequence in the seed sequence set with a window sequence obtained by the sliding window to determine the seed sequence capable of matching the reference sequence in the seed sequence set and the matching position of the seed sequence, wherein an error tolerance rate for the matching is $\varepsilon_1$.

4. A method as claimed in claim 3, wherein a step size of performing the sliding window is determined in accordance with L and $\varepsilon_1$.

5. A method as claimed in claim 3, wherein a distance between two adjacent entries of the reference library is greater than or equal to a step size of the sliding window.

6. A method as claimed in claim 1, further comprising matching each short fragment of the set of short fragments with a seed sequence corresponding to an entry of the reference library, wherein an error tolerance rate for the matching is $\varepsilon_2$.

7. A method as claimed in claim 1, further comprising after removing the subset of short fragments from the set of short fragments, removing a short fragment having a connectivity length less than a predetermined threshold, wherein the connectivity length is a total length of short fragments in a second alignment result that are from the read and are positioned to different entries of the reference library mapped to the reference sequence.

8. A method as claimed in claim 1, further comprising removing the read if the modified positioning result does not meet a predetermined requirement.

9. A method as claimed in claim 1, further comprising obtaining an extension sequence by extending the reconstructed sequence based at least partly on a common part of the reconstructed sequence and a reference sequence corresponding to the reconstructed sequence.

10. A method as claimed in claim 9, wherein the common part is a common substring.

11. A method as claimed in claim 10, further comprising:
finding the common sub string of the reconstructed sequence and the reference sequence corresponding to the reconstructed sequence, and determining a longest common substring of the reconstructed sequence and the reference sequence corresponding to the reconstructed sequence; and
extending the longest common substring based at least partly on an edit distance to obtain the extension sequence.

12. A method as claimed in claim 9, wherein the common part is a common subsequence.

13. A method as claimed in claim 12, further comprising:
finding the common subsequence of the reconstructed sequence and the reference sequence corresponding to the reconstructed sequence, and determining a longest common subsequence of the reconstructed sequence and the reference sequence corresponding to the reconstructed sequence; and
extending the longest common subsequence based at least partly on an edit distance to obtain the extension sequence.

14. A method as claimed in claim 11, further comprising:
truncating the extension sequence from at least one end of the extension sequence, calculating a proportion of error positioning sites of a truncated extension sequence, and stopping the truncating when the proportion of the error positioning sites of the truncated extension sequence is less than a third preset value.

15. A method as claimed in claim 11, further comprising:
i) obtaining a truncated extension sequence by calculating a first error rate and a second error rate,
wherein if the first error rate is less than the second error rate, truncating the extension sequence from a first end of the extension sequence, and
if the first error rate is greater than the second error rate, truncating the extension sequence from a second end of the extension sequence,
wherein the first error rate is a proportion of error positioning sites of the truncated extension sequence obtained by truncating the extension sequence from the first end of the extension sequence, and
the second error rate is a proportion of error positioning sites of the truncated extension sequence obtained by truncating the extension sequence from the second end of the extension sequence; and
ii) performing i) by replacing the extension sequence with the truncated extension sequence until the proportion of the error positioning sites of the truncated extension sequence is less than a fourth preset value.

16. A method as claimed in claim 11, further comprising:
performing a sliding window on the extension sequence from at least one end of the extension sequence, and calculating a proportion of error positioning sites of a window sequence obtained by the sliding window, and
truncating the extension sequence according to the proportion of the error positioning sites of the window sequence, and stopping the truncation when the proportion of the error positioning sites of the window sequence obtained by the sliding window is greater than a fifth preset value.

17. A method as claimed in claim 11, further comprising:
i) obtaining a truncated extension sequence by calculating a third error rate and a fourth error rate,
wherein if the third error rate is less than the fourth error rate, truncating the extension sequence from a second end of the extension sequence, and
if the third error rate is greater than the fourth error rate, truncating the extension sequence from a first end of the extension sequence, and
wherein the third error rate is a proportion of error positioning sites of a window sequence obtained by performing window sliding on the extension sequence from the first end of the extension sequence,
the fourth error rate is a proportion of error positioning sites of a window sequence obtained by performing window sliding on the extension sequence from the second end of the extension sequence; and
ii) performing i) by replacing the extension sequence with the truncated extension sequence until the proportion of the error positioning sites of the window sequence is greater than the sixth preset value.

18. A method as claimed in claim 16, wherein the window of the sliding window is no greater than a length of the extension sequence.

19. An alignment system, comprising:
one or more processors configured to execute a computer executable program, the executing the computer executable program comprising performing the method as claimed in claim 1; and
a storage device configured to store data, wherein the storage device comprises the computer executable program.

20. The method of claim 1, wherein the representations of individual seed sequences include at least one of a numeric or integer string.

21. An alignment device, comprising:
a processor;
memory configured to store a computer executable program that, when executed by the processor, performs operations comprising:
converting a read into a set of short fragments corresponding to the read;
accessing a reference library residing in the memory, wherein the reference library is a hash table constructed based at least partly on a reference sequence, the reference library comprises a plurality of entries, each entry of the reference library corresponds to a respective seed sequence, each seed sequence is capable of matching at least one sequence on the reference sequence, and representations of individual seed sequences are used as keys for the hash table to map to matching positions on the reference sequence,
wherein each seed sequence has a length L according to a total number of bases totalBase of the reference sequence, $L=\mu*\log(totalBase)$, $\mu \in [1, 3]$,
wherein a matching position of each seed sequence is determined by at least performing a sliding window on the reference sequence with a window having a size of L, and
wherein a distance on the reference sequence between two seed sequences that correspond to two adjacent entries of the reference library is less than a length of a short fragment;

generating a positioning result based at least partly on the accessed reference library, by at least inputting a representation of each short fragment of the set of short fragments as a key value to the hash table to retrieve a corresponding position on the reference sequence;

modifying the positioning result by removing a subset of short fragments from the set of short fragments, wherein each removed short fragment is selected from a respective group of short fragments in the set, whose positions correspond to adjacent entries of the reference library; and reconstructing a sequence based at least partly on the short fragments from the modified positioning result and their corresponding positions on the reference sequence, to obtain an alignment result of the read.

\* \* \* \* \*

UNITED STATES PATENT AND TRADEMARK OFFICE
CERTIFICATE OF CORRECTION

| | |
|---|---|
| PATENT NO. | : 11,482,304 B2 |
| APPLICATION NO. | : 16/635996 |
| DATED | : October 25, 2022 |
| INVENTOR(S) | : Weibin Xu et al. |

It is certified that error appears in the above-identified patent and that said Letters Patent is hereby corrected as shown below:

In the Claims

Column 18, Claim 2, Line 35:
"matching position of the seed sequence for each seed"
Should read:
--matching position for each seed--.

Column 19, Claim 11, Line 12:
"the common sub string of the"
Should read:
--the common substring of the--.

Signed and Sealed this
Fifteenth Day of October, 2024

Katherine Kelly Vidal
*Director of the United States Patent and Trademark Office*